United States Patent [19]

Mitomi

[11] Patent Number: 4,891,596

[45] Date of Patent: Jan. 2, 1990

[54] MAGNETIC RESONANCE IMAGING APPARATUS

[75] Inventor: Michio Mitomi, Ootawara, Japan

[73] Assignee: Kabushiki Kaisha Toshiba, Kawasaki, Japan

[21] Appl. No.: 203,099

[22] Filed: Jun. 7, 1988

[30] Foreign Application Priority Data

Jun. 11, 1987 [JP] Japan .................... 62-144058

[51] Int. Cl.$^4$ .............................. G01R 33/20
[52] U.S. Cl. ........................................ 324/318
[58] Field of Search ................ 324/309, 311, 318; 128/653

[56] References Cited

U.S. PATENT DOCUMENTS 4,725,779  2/1988  Hyde et al. .................. 324/318
4,817,612  4/1989  Akins et al. .................. 324/318

FOREIGN PATENT DOCUMENTS

P3819541.0-35  8/1989  Fed. Rep. of Germany .

OTHER PUBLICATIONS

I. R. Young et al., "Aspects of the Engineering Design of Whole-Body Nuclear Magnetic Resonance Machines", IEE Proceedings, vol. 134, Pt. A, No. 2, Feb. 1987, pp. 143–160.

P. Roschmann et al., "Die Bedeutung der HF-Spulen fur die Kernspintomographie The Importance of RF-Coils for the Magnetic Resonance Tomography", Biomed. Technik 31 (1968), pp. 178–185.

Primary Examiner—John Chapman
Assistant Examiner—Lawrence G. Fess
Attorney, Agent, or Firm—Foley & Lardner, Schwartz, Jeffery, Schwaab, Mack, Blumenthal & Evans

[57] ABSTRACT

A magnetic resonance imaging apparatus has a first surface coil for detecting a magnetic resonance signal induced in an object under examination. An induction current flows through the first surface coil by the magnetic resonance signal. A second surface coil is arranged to oppose the first surface coil through the object to be examined. The second surface coil is electrically endless. Therefore, a magnetic field is generated by the induction current. The magnetic field changes in accordance with a change in magnetic resonance signal. An eddy current flows through the second surface coil without flowing through the object to be examined in order to interfere with a change in magnetic field. As a result, an eddy current can be prevented from flowing through the object to be examined.

10 Claims, 6 Drawing Sheets

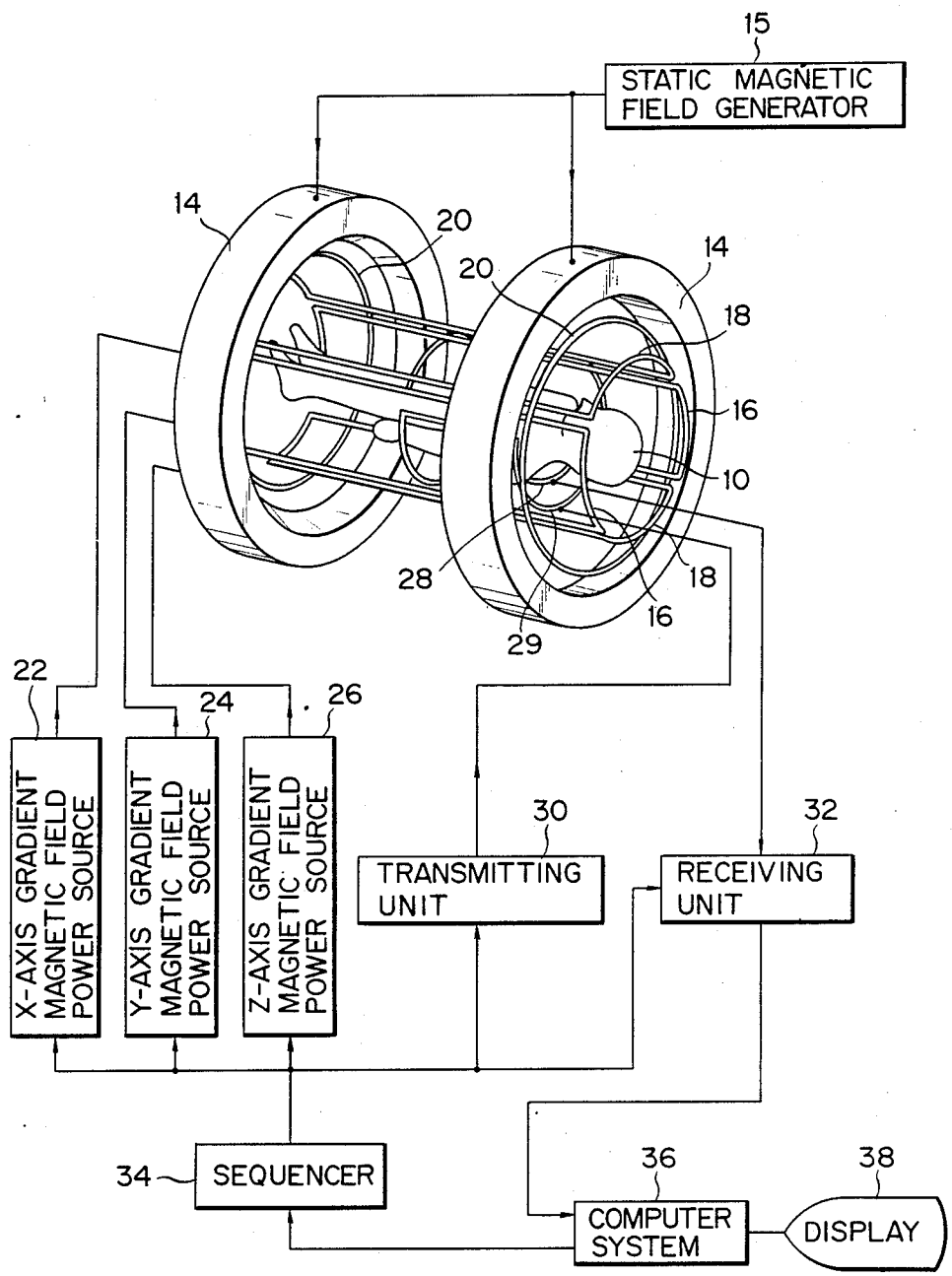
F I G. 2

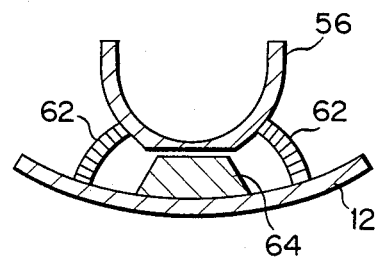
F I G. 9
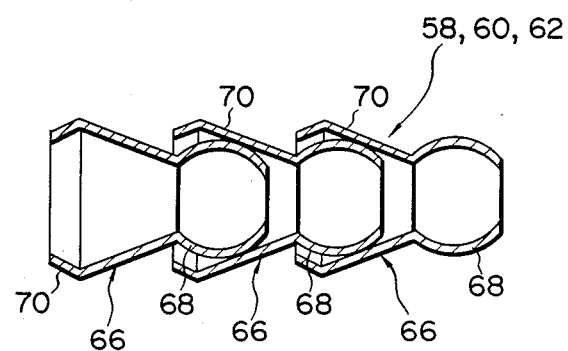
F I G. 10

MAGNETIC RESONANCE IMAGING APPARATUS

BACKGROUND OF THE INVENTION

1. Field of the Invention

The present invention relates to a magnetic resonance imaging apparatus for generating information such as a computed tomogram image in accordance with a computed tomography method from the density distribution of atomic nucleus spins in a specific portion of an object to be examined by utilizing a magnetic resonance phenomenon.

2. Description of the Related Art

For example, a magnetic resonance imaging apparatus for medical diagnosis has a bed for laying a patient to be examined thereon, a static magnetic field generator for generating a static magnetic field, gradient magnetic field generating coils for generating x-, y-, and z-axis gradient magnetic fields, a transmitting/receiving coil for transmitting/receiving a signal for generating a rotating magnetic field and for detecting an induced magnetic resonance signal, a static magnetic field power source for a static magnetic field generating coil, an x-axis gradient magnetic field power source for the x-axis gradient magnetic field generating coil, a y-axis gradient magnetic field power source for the y-axis gradient magnetic field generating coil, a z-axis gradient magnetic field power source for the z-axis gradient magnetic field generating coil, a transmitting/receiving unit for transmitting/receiving a transmission/reception signal to/from the transmitting/receiving coil, a sequencer for driving the x-, y-, and z-axis gradient magnetic field power sources and the transmitting/receiving unit with desired pulse sequences, and a computer system for controlling the above units and processing and displaying a detection signal.

The patient is laid on the bed and placed within a uniform magnetic field generated by the static magnetic field generator. In this state, the transmitting/receiving unit is driven by the pulse sequence obtained by the sequencer so that the transmitting/receiving coil applies, e.g., 90° and 180° pulses as the rotating magnetic field. At the same time, the x-, y-, and z-axis gradient magnetic field power sources are independently driven so that the x-, y-, and z-axis gradient magnetic field generating coils apply x-, y-, and z-axis gradient magnetic fields. As a result, magnetic resonance occurs in the patient. A magnetic resonance signal induced in the patient is detected by the transmitting/receiving coil. The detection signal is supplied to the computer system, and the computer system processes the signal to, e.g., reproduce the image. Thus, projection information of a predetermined slice of the patient is obtained. When the information is processed to reproduce the image, image information reflecting at least one of the spin density or relaxation time constant of a specific atomic nucleus of the patient is obtained.

Some such magnetic resonance imaging apparatuses use a surface coil as the transmitting/receiving coil for transmitting/receiving the magnetic resonance signal. The surface coil is arranged on the back of the patient. With this arrangement, a magnetic resonance signal from a tissue of the patient close to the surface coil can be received at a high sensitivity. Thus, this surface coil is effective when a magnetic resonance image concerning, e.g., the spinal cord of the patient is to be obtained.

However, because of the magnetic resonance signal from the patient, an induction current flows in the surface coil and forms a magnetic field. The magnetic field changes in accordance with the magnetic resonance signal. An eddy current flows in the patient's body to interfere with the change in magnetic field. When the eddy current flows in the patient's body, a magnetic reaction occurs to interfere with the change in magnetic flux, resulting in a poorer sensitivity distribution than expected. The sensitivity decreases rapidly as the distance between a target portion of the patient's body and the surface coil increases. As a result, when the portion to be examined is located at a deep portion within the patient's body, the sensitivity is insufficient.

SUMMARY OF THE INVENTION

It is an object of the present invention to provide a magnetic resonance imaging apparatus in which the reception sensitivity of a magnetic resonance signal can be increased.

According to an aspect of the present invention, there is provided a magnetic resonance imaging apparatus which a magnetic resonance imaging apparatus comprising a bed for laying an object to be examined thereon, static magnetic field generating means for generating a uniform static magnetic field at a desired portion of the object to be examine laid on said bed, gradient magnetic field generating means for generating a gradient magnetic field superposed on the static magnetic field generated by said static magnetic field generating means, means for supplying a rotating magnetic field to the object to be examined laid on said bed, receiving means for detecting a magnetic resonance signal induced by the object, and preventing means, formed to be electrically endless and arranged to oppose said receiving means through the object to be examined laid on said bed, for preventing an eddy current from flowing in the object to be examined.

BRIEF DESCRIPTION OF THE DRAWINGS

FIG. 2 shows the arrangement of a image pickup system used in the apparatus shown in FIG. 1;

FIG. 9 is a sectional view of the head rest portion;

FIG. 10 is a sectional view of a flexible member for supporting the first and second surface coils shown in FIG. 6;

DETAILED DESCRIPTION OF THE PREFERRED EMBODIMENT

A preferred embodiment of the present invention will be described with reference to FIGS. 1 to 5.

Figure 1:
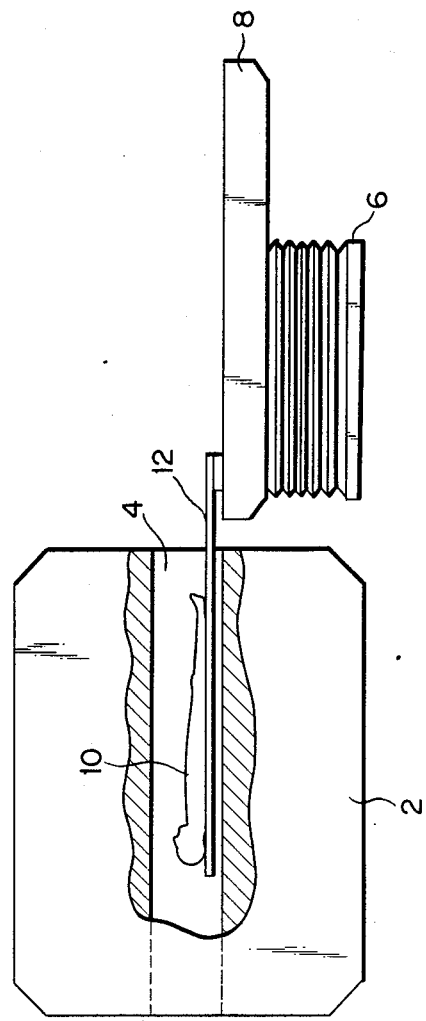
FIG. 1 is a front view of a magnetic resonance imaging apparatus according to the present invention.

Referring to FIG. 1, frame 2 incorporates an image pickup system. Hollow portion 4 is formed in the central portion of frame 2, and an image pickup region is formed in hollow portion 4.

Bed 6 is arranged adjacent to frame 2 and has elevating plate 8 which is vertically movable. Table 12 for laying patient 10 thereon is arranged on elevating plate 8. Table 12 is supported on plate 8 to be horizontally slidable from bed 6 into the image pickup region in frame 2.

The image pickup system has a pair of ring-shaped static magnetic field generating coils 14 for generating a uniform static magnetic field, as shown in FIG. 2. Coils 14 are connected to static magnetic field power source 15. X-, y-, and z-axis gradient magnetic field generating coils 16, 18, and 20 for generating x-, y-, and z-axis gradient magnetic fields, respectively, are arranged in a region defined inside coils 14. Coils 16, 18, and 20 are electrically connected to x-, y-, and z-axis gradient magnetic field power sources 22, 24, and 26, respectively.

Reference numeral 29 denotes a transmitting coil for transmitting a signal used for generating a rotating magnetic field. Reference numeral 28 denotes a first surface coil, which serves as a receiving coil for receiving a magnetic resonance signal induced in patient 10. Coil 28 is connected to receiving unit 32 for receiving a detection signal. Power sources 22, 24, and 26 and units 30 and 32 are connected to sequencer 34 to be driven with desired pulse sequences. Sequencer 3 receives a control signal from computer system 36. Computer system 36 receives a detection signal from receiving/transmitting unit 32. The detection signal is processed by computer system 36. Based on the processed detection signal, a tomographic image of patient 10 is displayed on display 38.

Figure 3:
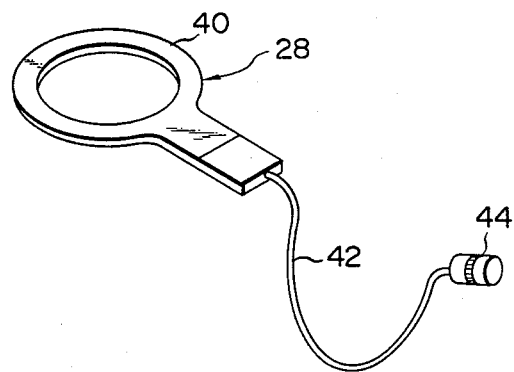
FIG. 3 shows a first surface coil shown in FIG. 4.

As shown in FIG. 3, first surface coil 28 has detecting section 40. Detecting section 40 is obtained by molding a ring-shaped coil (not shown) on a ring-shaped member of a resin or the like. Coil 28 is connected to one end of cable 42, and the other end of cable 42 is connected to connector 44. Coil 28 is detachably connected to the image pickup system through connector 44.

Figure 4:
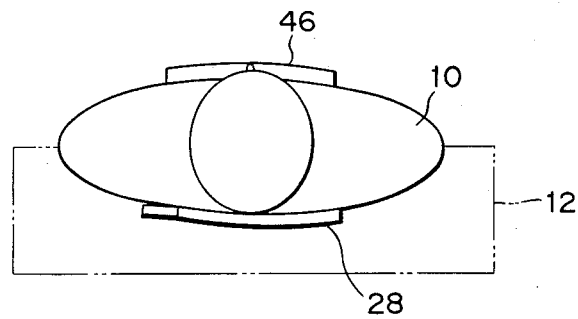
FIG. 4 shows the first and second surface coils of the apparatus shown in FIG. 1 in the used state.

As shown in FIG. 4, first surface coil 28 is arranged on the back of patient 10 in order to obtain a magnetic resonance image concerning, e.g., a bone marrow. In practice, second surface coil 46 is arranged to oppose first surface coil 28 through patient 10. When coil 28 is arranged between patient 10 and table 12, coil 46 is placed on patient 10.

Figure 5:
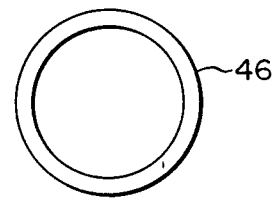
FIG. 5 is a plan view of the second surface coil shown in FIG. 3.
Figure 6:
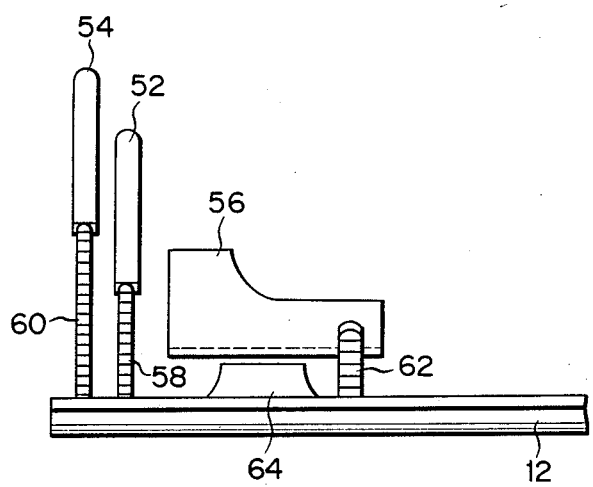
FIG. 6 is a side view showing a modification of the first and second surface coils.
Figure 7:
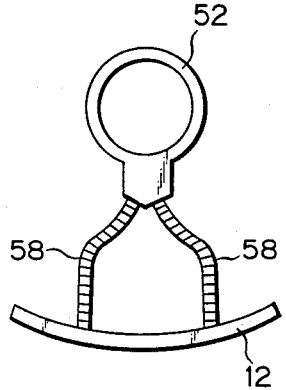
FIG. 7 is a front view of the first surface coil shown in FIG. 6.
Figure 8:
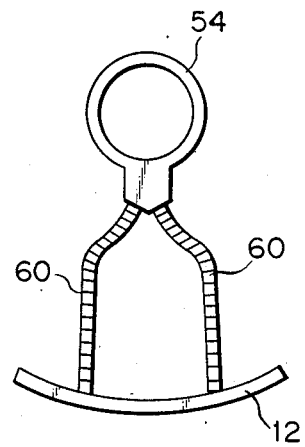
FIG. 8 is a front view of the second surface coil shown in FIG. 6.

As shown in FIG. 5, second surface coil 46 is obtained by molding an endless, circular conductive member (not shown) on a resin or the like.

Patient 10 is laid on table 12 of bed 6. Elevating plate 8 is moved upward and table 12 is slid. Thus, patient 10 is placed in a uniform magnetic field generated by static magnetic field generating coils 14 in the image pickup region of the image pickup system. In this state, transmitting unit 30 is driven by a pulse sequence of sequencer 34. 90° - and 180° - pulses as the rotating magnetic field are applied to patient 10 by transmitting coil 29. Simultaneously, x-, y-, and z-axis gradient magnetic field power sources 22, 24, and 26 are separately driven and x-, y-, and z-axis gradient magnetic fields are applied by x-, y-, and z-axis gradient magnetic field generating coils 16, 18, and 20, respectively. A magnetic resonance occurs in patient 10 and a magnetic resonance signal induced by the magnetic resonance phenomenon is detected by coil 28. The detection signal is fetched by computer system 36. Signal processing, e.g., image reconstruction is performed by computer system 36. Thus, projection information of a predetermined slice of patient 10 is obtained. When image reconstruction of the information is performed, image information reflecting at least one of a spin density and a relaxation time constant of a specific atomic nucleus is obtained.

In response to the magnetic resonance signal from patient 10, an induction current flows through first surface coil 28, and a magnetic field is formed by the induction current. This magnetic field changes in accordance with a change in magnetic resonance signal. An eddy current flows through second surface coil 46 without flowing through the body of patient 10 so as to interfere with the change in magnetic field. In other words, coil 46 serves as a shield to flow the eddy current through itself while it prevents the eddy current from flowing through the body of patient 10. As a result, the reception sensitivity of the magnetic resonance signal can be improved.

FIGS. 6 to 12 show modifications of the first and second surface coils.

In these modifications, first and second surface coils 52 and 54 and head rest 56 are mounted on one end of table 12 through pairs of flexible members 58, 60, and 62, respectively, as shown in FIGS. 6 to 9. First and second coils 52 and 54 are circular. Coil 52 serves as a receiving coil for detecting an induced magnetic resonance signal. Coil 54 prevents an eddy current from flowing through the body of patient 10. Head rest 56 is arcuated to have a U-shaped section, as shown in FIG. 9, so as to support the head of patient 10. Support 64 is provided on a portion of table 12 under head rest 56. Support 64 is made of a non-magnetic material and supports the weight of the head of patient 10 placed on head rest 56. Flexible members 58, 60, and 62 are obtained by sequentially coupling a plurality of plastic connection members 66 having the same shape, as shown in FIG. 10. More specifically, each connection member 66 has male and female coupling portions 68 and 70. When female coupling portion 70 of each connection member 66 and male coupling portion 68 of next connection member 66 are pivotally coupled, flexible member 58, 60, or 62 is formed.

Figure 11:
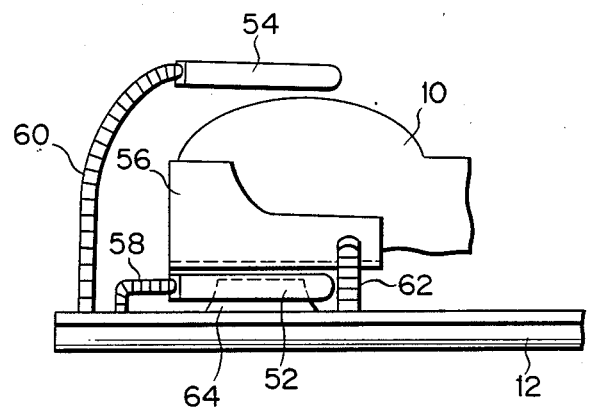
FIG. 11 is a side view showing another modification of the first and second surface coils.
Figure 12:
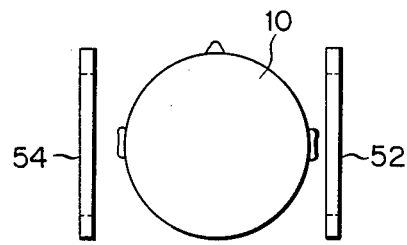
FIG. 12 shows a state wherein the first and second surface coils shown in FIG. 6 are used.

With the above-described arrangement, when flexible members 58, 60, and 62 are bent, first and second surface coils 52 and 54 can be easily caused to oppose each other through patient 10, as shown in FIGS. 11 or 12.

Second surface coil 46 or 54 is not limited to have a circular shape but can be of any type as long as it is endless.

What is claimed is:

1. A magnetic resonance imaging apparatus comprising:
   a bed for laying an object to be examined thereon;
   static magnetic field generating means for generating a uniform static magnetic field at a desired portion of the object to be examined laid on said bed;
   gradient magnetic field generating means for generating a gradient magnetic field superposed on the static magnetic field generated by said static magnetic field generating means;
   means for supplying a rotating magnetic field to the object to be examined laid on said bed;
   receiving means for detecting a magnetic resonance signal induced by the object; and
   preventing means, formed to be electrically endless and arranged to oppose said transmitting/receiving means through the object to be examined laid on said bed, for preventing an eddy current from flowing in the object to be examined.

2. The apparatus according to claim 1, wherein said preventing means has an endless coil for preventing the eddy current from flowing through the object to be examined.

3. The apparatus according to claim 2, wherein said coil is arranged in the vicinity of a surface of the object to be examined and has a surface coil for preventing the eddy current from flowing through the object to be examined.

4. The apparatus according to claim 1, wherein said preventing means is independently movable.

5. The apparatus according to claim 1, further comprising first support means for supporting said preventing means.

6. The apparatus according to claim 5, wherein said first support means has a first flexible member supporting said preventing means.

7. The apparatus according to claim 6, further comprising a second support means for supporting said receiving means.

8. The apparatus according to claim 7, wherein said second support means has a second flexible member for supporting said receiving means.

9. The apparatus according to claim 1, wherein said receiving means is arranged in the vicinity of a surface of the object to be examined and has another surface coil for detecting the magnetic resonance signal induced by the object.

10. A magnetic resonance signal detecting system of a magnetic resonance imaging apparatus, comprising:
   detecting means for detecting a magnetic resonance signal occurring in an object to be examined; and
   preventing means, formed to be electrically endless and arranged to oppose said detecting means through the object to be examined, for preventing an eddy current from flowing in the object to be examined.

* * * * *